(12) United States Patent
Reitsma

(10) Patent No.: US 6,261,276 B1
(45) Date of Patent: Jul. 17, 2001

(54) APPARATUS FOR DRAINING SURGICAL WOUNDS

(75) Inventor: Bert J. Reitsma, Manotick (CA)

(73) Assignee: I.S.I. International, Inc., Chicago, IL (US)

( * ) Notice: Subject to any disclaimer, the term of this patent is extended or adjusted under 35 U.S.C. 154(b) by 0 days.

(21) Appl. No.: 08/631,435

(22) Filed: Apr. 12, 1996

Related U.S. Application Data (63) Continuation-in-part of application No. 08/402,936, filed on Mar. 13, 1995, now abandoned.

(51) Int. Cl.$^7$ ............................................. A61M 1/00
(52) U.S. Cl. ........................................ 604/319; 128/765
(58) Field of Search .................... 604/317–322; 128/765

(56) References Cited

U.S. PATENT DOCUMENTS

| | | | |
|---|---|---|---|
| 2,963,256 | 12/1960 | Borah | 248/346 |
| 3,018,779 | * 1/1962 | Tyler et al. | 604/181 |
| 3,084,691 | * 4/1963 | Stoner | 604/134 |
| 3,376,868 | 4/1968 | Mondiadis | 128/278 |
| 3,836,287 | 9/1974 | Grosholz et al. | 417/306 |
| 3,908,664 | 9/1975 | Loseff | 128/350 R |
| 3,993,080 | 11/1976 | Loseff | 128/350 R |
| 4,397,643 | * 8/1983 | Rygiel | 604/317 |
| 4,569,674 | 2/1986 | Phillips et al. | 604/119 |
| 4,642,093 | 2/1987 | Härle | 604/54 |
| 4,655,754 | 4/1987 | Richmond et al. | 604/323 |
| 4,889,250 | 12/1989 | Beyer | 215/228 |
| 5,024,653 | * 6/1991 | Kohnke | 604/319 |
| 5,034,006 | 7/1991 | Hosoda et al. | 604/317 |
| 5,108,381 | 4/1992 | Kolozsi | 604/319 |
| 5,279,550 | 1/1994 | Habib et al. | 604/38 |
| 5,318,548 | * 6/1994 | Filshie | 604/319 |
| 5,429,623 | * 7/1995 | Dessel | 604/322 |

FOREIGN PATENT DOCUMENTS

| | | | | |
|---|---|---|---|---|
| 3502290 | * | 7/1986 | (DE) | 604/319 |
| 3637553 | * | 5/1988 | (DE) | 604/318 |
| 2150031A | | 6/1985 | (GB) | A61M/1/00 |
| 2235877A | | 3/1991 | (GB) | A61M/1/00 |
| 1431762 | * | 10/1988 | (RU) | 604/319 |

OTHER PUBLICATIONS

"The CRD System Catalog and Product Manual", Oct. 1981, cover page and p. 8, Author–Medi–Vac Corporation.*

A one page advertising brochure entitled "The Gish Orthofuser", by Gish Biomedical, Inc. dated 1995.

* cited by examiner

Primary Examiner—John G. Weiss
Assistant Examiner—Dennis Ruhl
(74) Attorney, Agent, or Firm—Gilhooly and Crossman

(57) ABSTRACT

Apparatus for draining surgical wounds is disclosed. One embodiment of the apparatus includes a disposable container to which a manual vacuum pump is releasably attached. The disposable container preferably includes an elastic bellows portion to provide a gauge of the subatmospheric pressure in the disposable container. The elastic bellows portion is preferably located in the neck of the container. The container may be rectangular or cylindrical. A suspension clamp for suspending the container from a bed sheet or a patient garment is also disclosed. Another embodiment of the container includes a vacuum chamber and a fluid collection chamber. The pump is in fluid communication with the vacuum chamber but isolated from the fluid collection chamber by a hydrophobic filter to prevent contamination of the pump with collected fluid. The advantages include an inexpensive, versatile, easy to operate wound drainage system which virtually eliminates the requirement for sterilization and the handling of wound drainage wastes, and the manual vacuum pump which may be operated to evacuate the container to any desired subatmospheric pressure which can be maintained or adjusted during postoperative use.

9 Claims, 10 Drawing Sheets

APPARATUS FOR DRAINING SURGICAL WOUNDS

RELATED APPLICATIONS

This is a Continuation-In-Part of U.S. patent application Ser. No. 08/402,936 filed Mar. 13, 1995, now abandoned.

TECHNICAL FIELD

The present invention relates to surgical wound drainage and, in particular, to apparatus for post operatively draining and collecting fluids from a closed surgical wound.

BACKGROUND OF THE INVENTION

It has long been recognized that large surgical wounds are advantageously drained of fluids to facilitate healing and improve the readaptation of tissue layers surrounding the wound. Considerable effort has therefore been invested in designing devices to provide consistent and effective drainage of surgical wounds by partially evacuated collection containers which promote surgical wound drainage.

Such devices may be generally divided into three categories, compressible containers, electric vacuum machines and precharged disposable containers. All three categories of wound drainage devices operate on the principle that a partial vacuum provides suction in the surgical wound to promote the drainage of fluids from the wound. The first category includes simple mechanical devices which are spring biased collapsible containers or containers with elastic memory. Both are generally made of resilient elastomeric material. Such containers are manually compressed to provide suction for removing and collecting fluids from surgical wounds. One example of this type of device is disclosed in U.S. Pat. No. 3,993,080 to Loseff which issued Nov. 23, 1976. Such devices suffer from certain drawbacks. First, such devices have a limited capacity for providing suction, the amount of suction provided being related to the elasticity and the volume of the container. Second, they generally provide no means for monitoring the subatmospheric pressure in the container. It is therefore difficult to judge how much suction is being applied to a wound, and the quality of the vacuum may deteriorate as the container loses its elastic memory over time. Third, such containers collect the fluid drained from the wound and must therefore be discarded after use or emptied, cleaned and sterilized, with all the attendant hazards and time consuming activity involved in handling medical waste.

The second category of wound drainage devices includes the vacuum machines equipped with electrically powered vacuum pumps which are generally controlled by electronic circuits that poll sensors to monitor vacuum levels. Examples of such devices are disclosed in U.S. Pat. No. 4,569,674 to Phillips et al. which issued Feb. 11, 1986, and U.S. Pat. 3,836,287 to Grosholz et al. which issued Sep. 17, 1974. These are complex, expensive machines which may also be used as wound irrigation devices. Some of these machines accumulate fluid in disposable containers (see U.S. Pat. No. 3,836,287) to minimize maintenance. The disadvantages of such machines are that they are generally bulky, most are unusable by ambulatory patients, and they are expensive to manufacture and maintain.

The third category of such devices includes lightweight molded plastic or glass containers which are pre-evacuated to provide either a "high" (about 0.9 bar) or a "low" (about 0.4 bar) vacuum. For example, see U.S. Pat. 4,642,093 to Harle which issued Feb. 10, 1987. These containers are transportable and are usually disposable. Some also include a gauge to indicate whether there is negative pressure in the container. Some of the disadvantages of these devices are that they are useless once the vacuum has been discharged from the container, do not provide adjustable vacuum, and do not provide consistent vacuum over an extended period of time. They also do not permit an optimal regimen for surgical wound drainage whereby the suction force is regulated over time to optimize the readaptation of tissue surrounding the wound. Furthermore, these containers must be carefully handled to ensure that the vacuum is not released before they are used because they provide no mechanism for recharging the vacuum once it is discharged.

Surgical wounds requiring drainage may be located in either "soft tissue", such as found in the abdominal cavity, or in "hard tissue", such as striated muscle. It has long been recognized that these two types of tissue require different treatments to ensure that the tissues surrounding the surgical wound are optimally readapted and healing is facilitated. Soft tissues should not be subjected to high vacuums for prolonged periods of time, i.e. suction forces in excess of about 0.5 bar, while hard tissue is preferably subjected to higher vacuum for effective drainage. Hence, precharged wound drainage containers are offered in low pressure and high pressure units, as described above.

It has also been discovered that optimal post-operative results are generally achieved if a regimen is followed in which the suction force for surgical wound drainage is varied over time. The amount of suction for optimal results depends on the type tissue in which the wound is located, as well as the time that has elapsed since the wound was created. It is therefore desirable to provide an apparatus for draining surgical wounds which permits the subatmospheric pressure for promoting drainage to be monitored and adjusted in accordance with an optimal regimen.

It is also known that the suction force provided by most apparatus for draining surgical wounds decreases proportionally with the volume of fluid collected. In other words, as fluid is drained from a wound, the suction forte applied by the container is proportionally reduced. It is therefore desirable to provide a container in which the vacuum can be adjusted to an optimal level until the container has collected its nominal capacity of fluid, or the container is no longer needed.

The spread of blood-borne diseases such as AIDS and Hepatitis-C have also heightened awareness of the value of blood products. It has therefore been recognized that in certain circumstances it may be inappropriate to dispose of wound drainage fluids if they can be used for transfusion back into a post-operative patient. It is therefore desirable to provide a wound drainage collection apparatus which is adapted to collect wound drainage fluids in a container such as a blood bag which permits the fluids to be used for transfusion, if appropriate.

There therefore exists a need for a simple, easy to use, inexpensive wound drainage system that overcomes these known disadvantages of the prior art, and is adapted to permit one to follow an optimal post-operative wound drainage regimen.

SUMMARY OF THE INVENTION

It is an object of the invention to provide a simple surgical wound drainage apparatus for removing and collecting fluids from a closed wound which is inexpensive to manufacture.

It is another object of the invention to provide a simple surgical wound drainage apparatus which provides an inexpensive, safe, disposable collection container for wound drainage wastes.

It is a further object of the invention to provide a simple surgical wound drainage apparatus which provides adjustable and rechargeable vacuum using a hand-operated vacuum pump.

It is yet a further object of the invention to provide a simple surgical wound drainage apparatus which provides a gauge of the subatmospheric pressure in the collection container.

It is another object of the invention to provide an inexpensive surgical wound drainage apparatus which permits the suction force to be regulated over time to facilitate an optimal regimen of surgical wound drainage.

It is yet another object of the invention to provide an inexpensive surgical wound drainage apparatus which permits the collection of wound drainage fluids in a container adapted to permit the fluid to be transfused back into the patient, if appropriate.

In its simplest form, the apparatus in accordance with the invention comprises a plastic container, preferably manufactured from polyethylene, having a sidewall that defines a substantially rigid wound drainage waste collection reservoir located at the bottom of the container and an elastic bellows gauge located above the reservoir. The bellows gauge is preferably incorporated into the neck of the container. Wound drainage waste is collected in the reservoir and disposed of with the container, which is closed by a cap after the container is full or wound drainage is completed and the vacuum pump is removed from the container. An indication of the subatmospheric pressure in the container is preferably provided by the position of a lower end of the vacuum pump with respect to an index on the sidewall of the container. The index may be printed or molded oil the container sidewall to provide a quantitative indication of the negative pressure in the container. The container is provided with at least one connector for connecting a wound drainage tubing in a fluid tight relationship to the container. The container preferably has a neck with a screw thread connector to permit the fluid tight connection of a hand-operated vacuum pump and a screw cap to close the container for disposal.

The surgical wound drainage apparatus in accordance with the invention is also preferably provided with a suspension clamp for suspending the container from a bed sheet, a patient gown or the like so that ambulatory patients and patients in transfer can benefit from controlled vacuum assisted wound drainage.

In accordance with another embodiment of the invention, there is provided a two-chambered container for draining surgical wounds. A first chamber serves as a drainage fluid collection chamber while the second chamber serves as a vacuum chamber to which a hand operated vacuum pump is connected. The hand operated vacuum pump and the vacuum chamber are preferably interconnected by a fluid communication path which includes a hydrophobic and bacteriostatic filter to prevent redound drainage fluids from entering the pump and to inhibit contamination of the atmosphere with airborne infectious agents. The container is also preferably provided with a bellows gauge for indicating the subatmospheric pressure in the collection chamber. The vacuum chamber is preferably provided with a vacuum release valve which permits a user to regulate the pressure in the collection chamber. The advantages of this apparatus are two-fold. First, the first apparatus permits an optimal suction force to be maintained in the surgical wound, and even if the collection chamber is substantially full to its nominal capacity. Second, the apparatus permits an optimal regimen for wound drainage to be followed, wherein the suction force is maintained at an optimal level that varies over time.

A further embodiment of the invention provides a two-chambered container which is closed by a removable cover. This container also includes a vacuum chamber and a drainage fluid collection chamber. The drainage fluid collection chamber, however, is adapted to receive a blood bag for collecting the fluid drained from the surgical wound. This permits all or part of the collected fluid to be reinfused in the patient should circumstances warrant.

BRIEF DESCRIPTION OF THE DRAWINGS

The invention will now be explained by way of example only and with reference to the following drawings, wherein:

FIG. 9a shows yet a further configuration for a preferred embodiment of the container for a surgical wound drainage apparatus in accordance with the invention wherein the container is reusable and includes two chambers, a first chamber for housing the manual pump and a second chamber for housing a blood bag which receives and contains wound drainage fluid so that the fluid may be disposed of or used for transfusion back to the patient when appropriate;

FIG. 9b shows a side elevational view of the container shown in FIG. 9a;

FIG. 10b shows a cross-sectional view of the container shown in FIG. 10a;

DETAILED DESCRIPTION OF THE PREFERRED EMBODIMENT

A first embodiment of the surgical wound drainage apparatus in accordance with the invention includes a disposable container and a manual vacuum pump for evacuating the container, as well as a suspension clamp for suspending the container from a support and an optional stabilizer base for supporting the container on a flat surface.

Figure 1A:
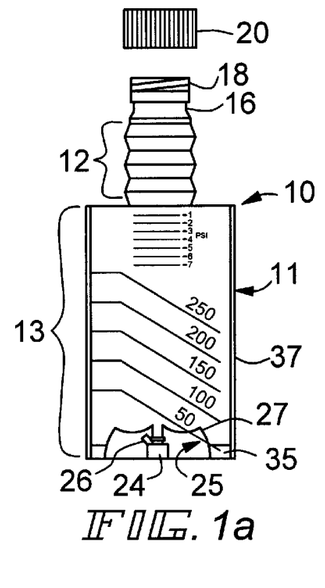
FIG. 1a is a side elevational view or a first configuration for a preferred embodiment of a container for the surgical wound drainage apparatus in accordance with the invention.

FIG. 1a illustrates a first configuration for a preferred embodiment of a container 10 in accordance with the invention. The container 10 is square or rectangular and preferably has a capacity of about 300 ml. The container 10 is preferably a disposable plastic bottle molded from a polymer such as polyethylene in a manner well known in the art. The container 10 includes a sidewall 11 and a neck 16. The neck 16 includes a resilient compressible bellows gauge 12 which compresses as the container is evacuated to a subatmospheric pressure, as will be explained below with reference to FIG. 1c.

The neck 16 has a standard thread 18 for securing a disposable cap 20 of a type used for plastic carbonated beverage bottles. The container 10 is also provided with a connector 22 adapted for the attachment of a wound drainage tubing. The connector 22 is located in the bottom of the container 10, is explained in more detail below. The shape and configuration of the connectors 22 are well known in the art. The connectors contain a one-way valve (not illustrated) to prevent back flow in case the wound drainage tubing is accidentally disconnected from the container 10. The connector 22 is preferably adapted to accept wound drainage tubing connectors of the Luer Lock® system which are readily commercially available from medical suppliers. The connector 22 is provided with a cap 24 which is secured to the connector 22 by a strap 26. The cap 24 closes the connector 22 and provides a seal which is fluid impervious to a subatmospheric pressure of at least –0.9 atmospheres. As is apparent, the container 10 preferably includes a volume scale printed or embossed on the sidewall 11 to indicate the amour it of wound drainage fluid collected in the container 10. For reasons that will be explained below in reference to FIG. 7, the volume scale is preferably arranged to be read when the container is in either an upright position, or a suspended position in which it is inclined at an angle.

Figure 1B:
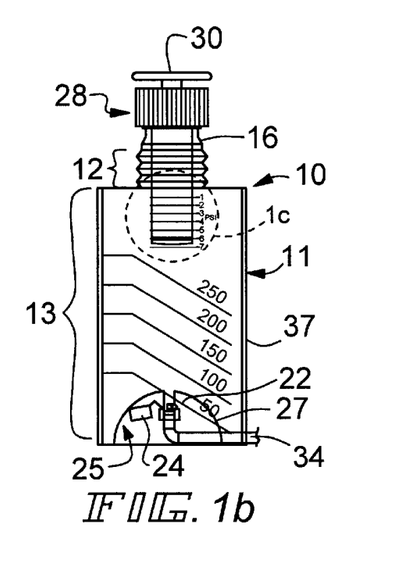
FIG. 1b shows the container illustrated in FIG. 1a with a manual vacuum pump attached to the neck of the container, and a wound drainage tube connected to the container, an elastic bellows portion of a neck of the container indicating that the interior of the container is at subatmospheric pressure.

FIG. 1b shows the container 10 illustrated in FIG. 1a with a manual vacuum pump 28 attached to the neck 16 of the container. The manual vacuum pump is preferably of a type described in U.S. Pat. No. 4,889,250, which is incorporated herein by reference. The manual vacuum pump 28 includes a handle 30 used to operate a piston for evacuating the container 10 during use. FIG. 1b shows the container 10 after it has been evacuated to a subatmospheric pressure. As is apparent, the resilient, compressible bellows gauge 12 of the container neck 16 has been compressed by the vacuum in the container 10. The bellows gauge 12 is corrugated and has an elastic memory which continually urges it to assume its original shape. The elasticity of the corrugated sidewall of the bellows gauge 12 is preferably such that the corrugations are completely compressed when the subatmospheric pressure in the container 10 is at about –0.5 atmosphere (–7.3 psi or 380 TORR). The subatmospheric pressure is preferably indicated by a pressure scale that is printed or embossed on the sidewall 11 so that a bottom end of the vacuum pump 28 indicates the subatmospheric pressure in the container. As may be seen in FIG. 1c, the subatmospheric pressure is indicated in PSI (pounds per square inch), although a scale in atmospheres or TORR could also be used.

Figure 1C:
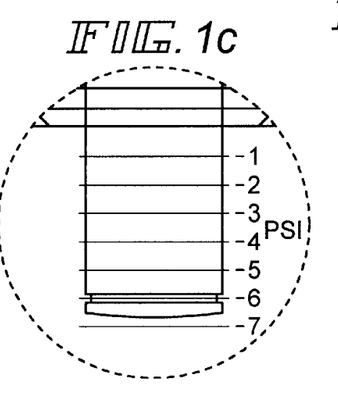
FIG. 1c shows an exploded view of scale for indicating the subatmospheric pressure in the container shown in FIG. 1b.

A feature of the first preferred embodiment of the container 10 shown in FIGS. 1a–c is the placement of the connector 22 for the wound drainage tubing 34 (see FIG. 1b) which is located in a bottom of the container. The location of the connector 22 provides a stable container which is not prone to tipping while resting on a flat surface. Provided in the bottom of the container is a dome-shaped recess 25 which includes a molded flexure groove 27 that permits the wall of the recess 25 to be pulled downwardly (see FIG. 1a) to facilitate the connection of a wound drainage tubing 34. After the tubing 34 is connected to the connector 22, the wall of the recess 25 is pushed upwardly (see FIG. 1b) to provide a stable base for the container 10.

Figure 1D:
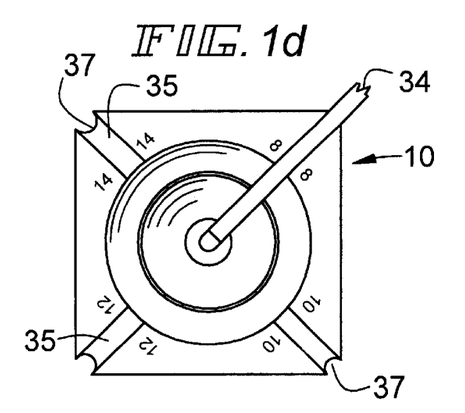
FIG. 1d shows a bottom plan view of the container illustrated in FIG. 1b with the wound drainage tube connected to the container.
Figure 1E:
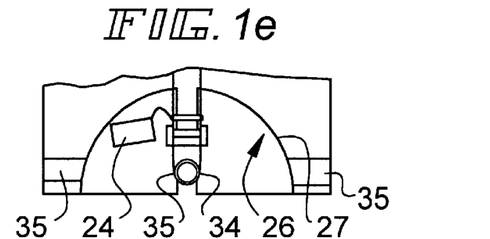
FIG. 1e is an enlarged view of a bottom end of the container shown in FIGS. 1a–b, to illustrate the shape of the groove which retains a wound drainage tubing.

FIG. 1d illustrates a bottom plan view of the container 10 shown in FIGS. 1a–b. Located in each corner of the container 10 is a slot 35. Each of the slots 35 is of a different size. The slots 35 are respectively adapted to receive a wound drainage tubing 34 of 8, 10, 12 or 14 (Charriere or C. scale) in an interference fit which locks the tubing 34 in a slot 35. FIG. 1e shows an enlarged view of a slot 35 located in each corner of the container 10. Each slot 35 preferably comprises a narrow neck region which communicates with a cylindrical slot sized to accommodate a wound drainage tubing 34 of a particular size. Once forced into the slot 35, the wound drainage tubing 34 is retained securely within the slot 35. Molded vertically along each corner of the container 10 is an elongated slot 37 of a corresponding size to accommodate a tubing 34 of the same gauge when the container is in a suspended position (see FIG. 7). The elongated slots 37, as well as securing the tubing 34 also reinforce the sidewalls 11 of the container and consequently reduce the amount of plastics material required to construct the walls of the container 10.

FIGS. 2a–d illustrate a second preferred embodiment of a container 10 in accordance with the invention. In this embodiment, the resilient, compressible bellows portion 12 of the container 10 is also located in the neck 16 of the container 10 but the container 10 is cylindrical in shape. With this configuration of the container 10, a subatmospheric pressure scale can likewise be printed or molded on the sidewall 11, and the pressure scale is also easily read.

Figure 2A:
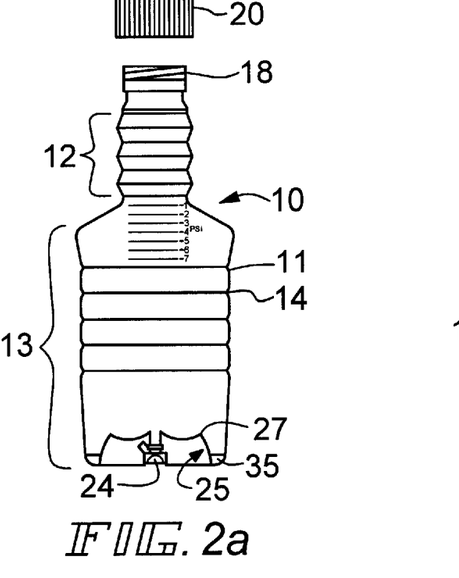
FIG. 2a shows an alternate configuration for the container in accordance with the invention wherein the container is cylindrical and the elastic bellows portion is also incorporated in the neck of the container.
Figure 2B:
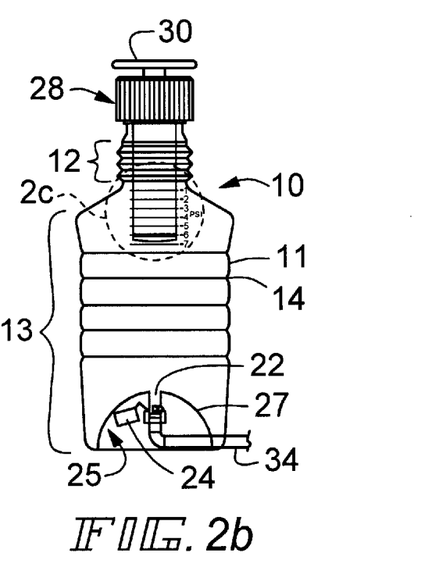
FIG. 2b shows the container illustrated in FIG. 2a with a manual vacuum pump attached to the neck of the container, and a wound drainage tube connected to the container, an elastic bellows portion of a neck of the container indicating that the interior of the container is at subatmospheric pressure.
Figure 2C:
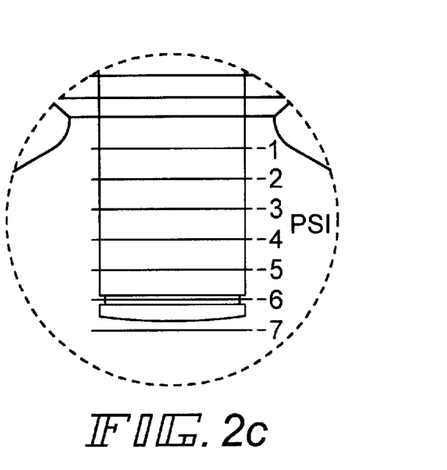
FIG. 2c shows an exploded view of an index for indicating the subatmospheric pressure in the container shown in FIG. 2b.

FIG. 2b illustrates the container 10 shown in FIG. 2a evacuated to a subatmospheric pressure. As is apparent, the compressible bellows portion 12 is compressed by the subatmospheric pressure in the container 10. The enlarged view of the subatmospheric scale shown in FIG. 2c illustrates how the bottom end of the vacuum pump 28 is used to indicate the subatmospheric pressure in the container 10, as explained above.

Figure 2D:
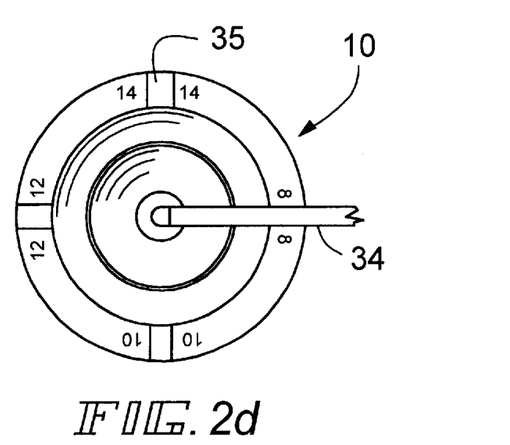
FIG. 2d shows a bottom plan view of the container illustrated in FIG. 2b.
Figure 3A:
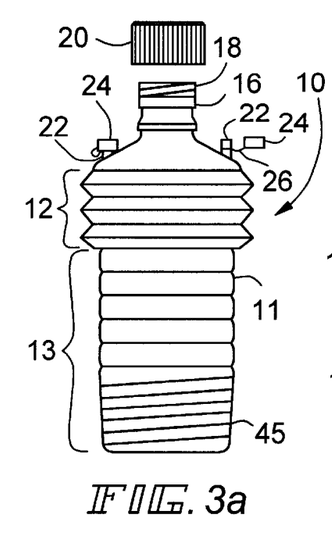
FIGS. 3a–c are elevational views of another configuration for a preferred embodiment of a container for the surgical wound drainage apparatus in accordance with the invention, the container shown in FIG. 3a having a capacity of 350 ml, the container shown in FIG. 3b having a capacity of 250 ml and the container shown in FIG. 3c having a capacity of 150 ml.

FIG. 2d shows a bottom plan view of the container 10 shown in FIG. 3a. As is apparent, a bottom rim of the container 10 includes 4 inverted keyhole-shaped slots respectively sized to receive 8, 10, 12 and 14 Charriere wound drainage tubing in an interference fit that locks the tubing in an appropriate slot. This arrangement for the placement of the connector 22 can of course be incorporated into other configurations of the container described below and can be used, for instance, to replace the connector 22 shown on those containers illustrated in FIGS. 3a–c, or vise versa.

Figure 3B:
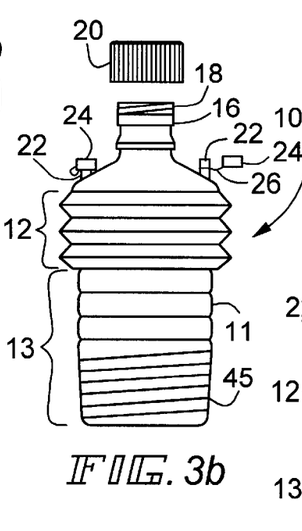
Figure 3C:
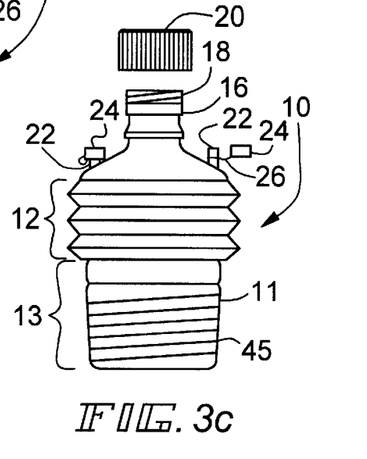

FIGS. 3a–c illustrate another configuration for a preferred embodiment of a container 10 in accordance with the invention. The containers illustrated in FIGS. 3a–c are identical except for the capacity of a collection reservoir 13 located at the bottom of each container. The container shown in FIG. 3a preferably has a collection reservoir with a capacity of about 350 ml. The collection reservoir of the container shown in FIG. 3b preferably has a capacity of about 250 ml and the collection reservoir of the container shown in FIG. 3c preferably has a capacity of about 150 ml. Each container may be manufactured in the same mold, with mold inserts being used to produce the two containers of smaller capacity, in a manner well known in the art.

Figure 4A:
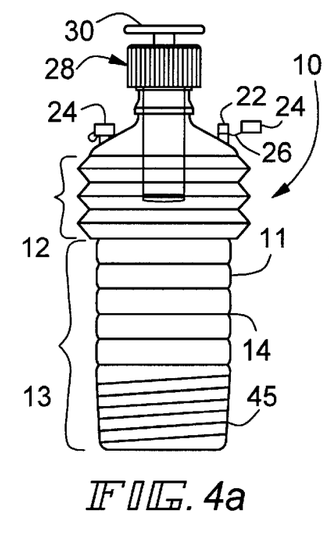
FIG. 4a shows the container illustrated in FIG. 3a with a manual vacuum pump attached to the neck of the container, an elastic bellows portion of a sidewall of the container indicating that the interior of the container is at atmospheric pressure.
Figure 4B:
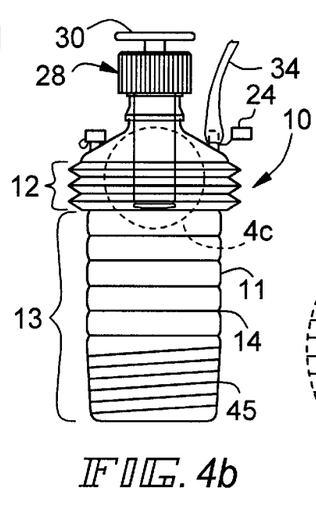
FIG. 4b shows the container illustrated in FIG. 4a with a wound drainage tube connected to the container, and the elastic bellows portion of the sidewall indicating that the interior of the container is at subatmospheric pressure.
Figure 4C:
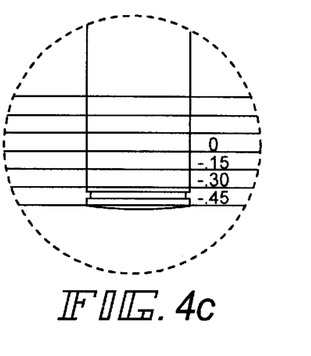
FIG. 4c is an exploded view of a scale for indicating the subatmospheric pressure in the container shown in FIG. 4b.

In each embodiment shown in FIGS. 4a–c, the container includes a sidewall 11 having a resilient, compressible bellows portion 12 and a substantially rigid lower portion which defines the collection reservoir 13. The collection reservoir 13 is preferably reinforced with corrugations 14 for minimizing the material required to construct the sidewall of the container. Corrugations 14 are optional. It is preferable, however, that the collection reservoir 13 of the sidewall is adapted to contain a subatmospheric pressure of at least –0.9 atmospheres (about –13.2 psi or 76 TORR) without collapsing. The bottom of the sidewall 11 also preferably includes an external spiral thread 45 for securing the container 10 in a stabilizer base, as will be explained below with reference to FIG. 5a–b.

FIGS. 4a–c illustrate the container 10 shown in FIGS. 3a–c with a manual vacuum pump 28 attached to the neck 16 of the container.

The container 10 shown in FIG. 4b has been connected to a wound drainage tube 34 and partially evacuated using the manual vacuum pump 28. The elastic bellows gauge 12 of the sidewall 11 provides at least a qualitative indication of negative pressure in the container. As shown in FIG. 4b, the elastic bellows gauge 12 is compressed when the container is evacuated. The bellows gauge 12 thereby provides a qualitative measure of the vacuum, and to an experienced observer, an approximate quantitative gauge of subatmospheric pressure. Alternatively, as described above, a subatmospheric pressure index may be molded or printed onto the bellows gauge 12 (see FIG. 4c) to provide a quantitative measure of the vacuum in the container 10. The bottom end of the vacuum pump 28 indicates the approximate subatmospheric pressure, in atmospheres, in the container when aligned with the scale on the sidewall 11 of the container 10. The scale could also be adapted to indicate the subatmospheric pressure in units of psi as shown in FIGS. 1b and 2b, or TORR.

Figure 5A:
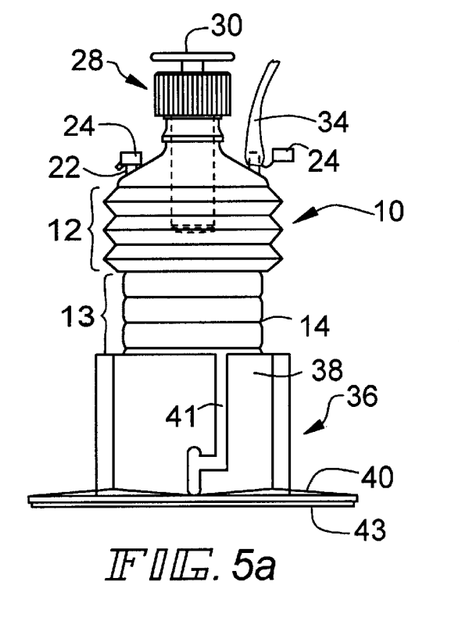
FIG. 5a shows the container illustrated in FIG. 4a supported in a stabilizer base for supporting the container on a flat surface.

FIG. 5a shows the cylindrical configuration of the container 10 supported in a stabilizer base 36 for preventing the container 10 from tipping when placed on a flat surface. The stabilizer base 36 includes a base plate 40, preferably a disc to which is affixed a sleeve 38 sized to receive a bottom end of the collection reservoir 13 of the container 10. The base plate 40 may be adhered to a flat surface, such as a bedside stand, with a double-sided adhesive tape 43 to provide an even more secure support for the container 10. To accommodate the container 10 shown in FIGS. 2a–c, the sleeve 38 includes a vertical slot 41 to accommodate a drainage tubing 34 attached to a connector located at a bottom of the container 10 shown in FIG. 2b. The vertical slot 41 is preferably Z-shaped near the bottom of the cylindrical sleeve 38 so that the wound drainage tubing 34 (see FIG. 2b) locks the container 10 in the stabilizer base 36.

Figure 5B:
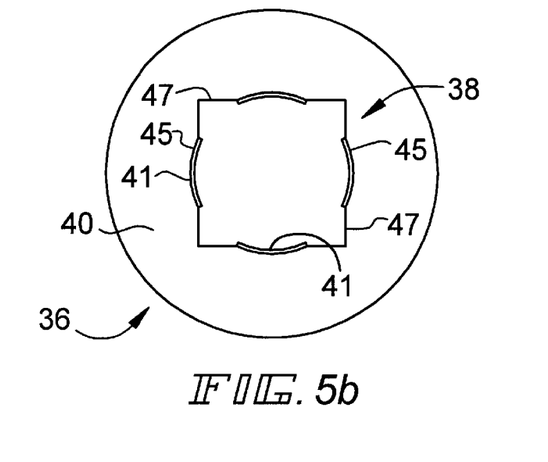
FIG. 5b is a top plan view of the stabilizer base shown in FIG. 5a, to illustrate the shape of a base designed to support both square and cylindrical containers.

FIG. 5b shows a plan view of the stabilizer base 36 configured to support the square embodiment of the container shown in FIG. 1a, and the cylindrical embodiment shown in FIGS. 2a and 3a. The sleeve 38 includes V-shaped corners 47 to accommodate square containers and cylindrical sections interleaving the V-shaped corners 47 to support cylindrical containers. An internal spiral thread 45 on the inner side of the cylindrical sections of the sleeve 38 engage the external thread on the sidewall 11 of the container 10 shown in FIGS. 3a–c to lock that embodiment of the container securely in the stabilizer base 36.

Figure 6:
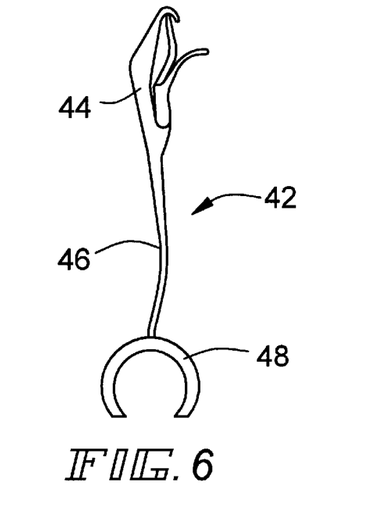
FIG. 6 shows a preferred suspension clamp for suspending the surgical wound drainage containers so that the apparatus may be used by patients who are ambulatory or in transit.

FIG. 6 shows a suspension clamp for suspending a container 10 so that the surgical wound drainage system can be used by ambulatory patients, or suspended from a bed sheet, a patient gown or the like in an instance when a patient is in transit or where supporting the container on a level surface is not practical or convenient.

The suspension clamp shown in FIG. 6 is preferably molded in one piece from a resilient plastic material. The suspension clamp 42 includes a clamp portion 44 which is adapted to be useful for gripping cloth material or the like, as will be explained in more detail below. A flexible connector 46 may be a round or flat cord-shaped extrusion which is preferably integral with a container gripping portion 48 and the clamp portion 44. The container gripping portion 48 is substantially C-shaped and sized to securely grip the neck 16 of the container 10 (see FIG. 7) after it is forced over the neck 16 from a side of the neck by manual pressure.

Figure 7:
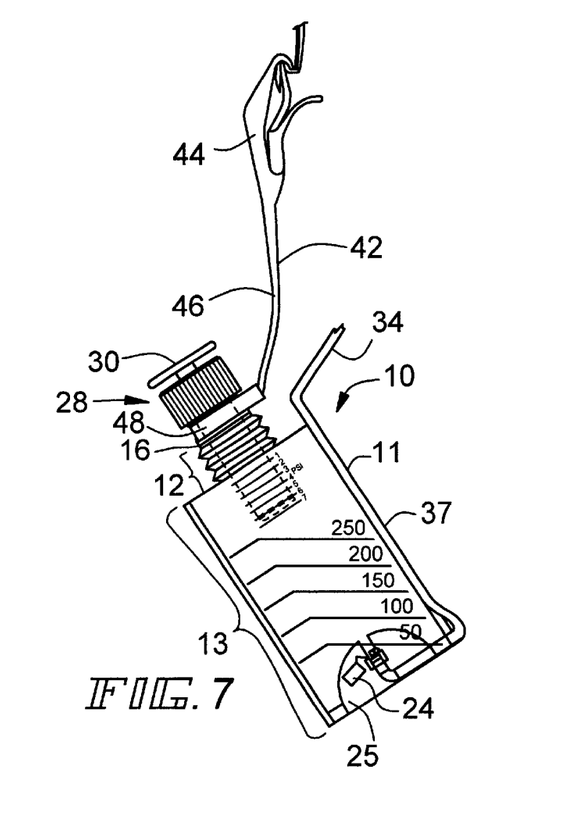
FIG. 7 illustrates the suspension clamp shown in FIG. 6 in use.

As shown in FIG. 7, a container 10 is supported in a suspended position using the suspension clamp 42. The container gripping portion 48 grips the neck of the container while the clamp portion 44 is clamped to a fabric 50 such as a bed sheet, a towel, a patient gown or a bath robe. This permits the wound drainage system to be used in conditions where there is no support surface for supporting the container 10, such as during patient transport from the operating room, in a recovery room, or when the patient is ambulatory. It may also be preferable to be able to suspend the container 10 if a surgical wound is in a part of the body which is subject to frequent movement, such as an arm or a leg.

In use, a surgical wound drainage tubing 34 is implanted in the surgical wound in a manner well known in the art and the wound drainage tubing 34 is connected to the connector 22 (see FIGS. 2b, 4b). The vacuum pump 28 is then manually operated by raising and lowering the handle 30 to evacuate the container 10. The subatmospheric pressure in the container 10 is indicated by the compression of the bellows gauge 12. A desired or target subatmospheric pressure depends on the type of tissue surrounding the surgical wound, its location and the required duration of suction. After a target subatmospheric pressure is established in the container 10, the container may be readily monitored and the target subatmospheric pressure may be maintained by occasional operation of the manual vacuum pump 28, as necessary.

The advantage of the apparatus is that it is adapted to provide a wide range of subatmospheric pressures which are readily monitored and maintained by nursing staff and/or the patient. A further advantage is that the vacuum pump, when the system is properly used, is not contaminated by fluids drained from the surgical wound. When a container 10 is filled to nominal capacity or drainage of the wound is completed, the disposal procedure is somewhat different for the different configurations of the container 10. For the first and second embodiment, the vacuum pump 28 is removed from the container 10 and a closure cap 20 is placed on the container 10. The container 10 is then inverted, the wound drainage tube 34 is detached from connector 22 (see FIG. 1b, 2b), the connector 22 is sealed with the cap 24 and the container is disposed of. For the third embodiment, the wound drainage tubing 34 is disconnected from the connector 22 (see FIG. 1c) and the connector 22 is sealed using the cap 24. The vacuum pump 28 is detached from the container 10, a closure cap 20 is placed on the container 10, and the container is disposed of.

Since the container 10 is made from an inexpensive plastic material, a very economical and useful apparatus is provided which eliminates the complications of using prior art vacuum drainage systems for surgical wounds.

Figures 8A, 8B:
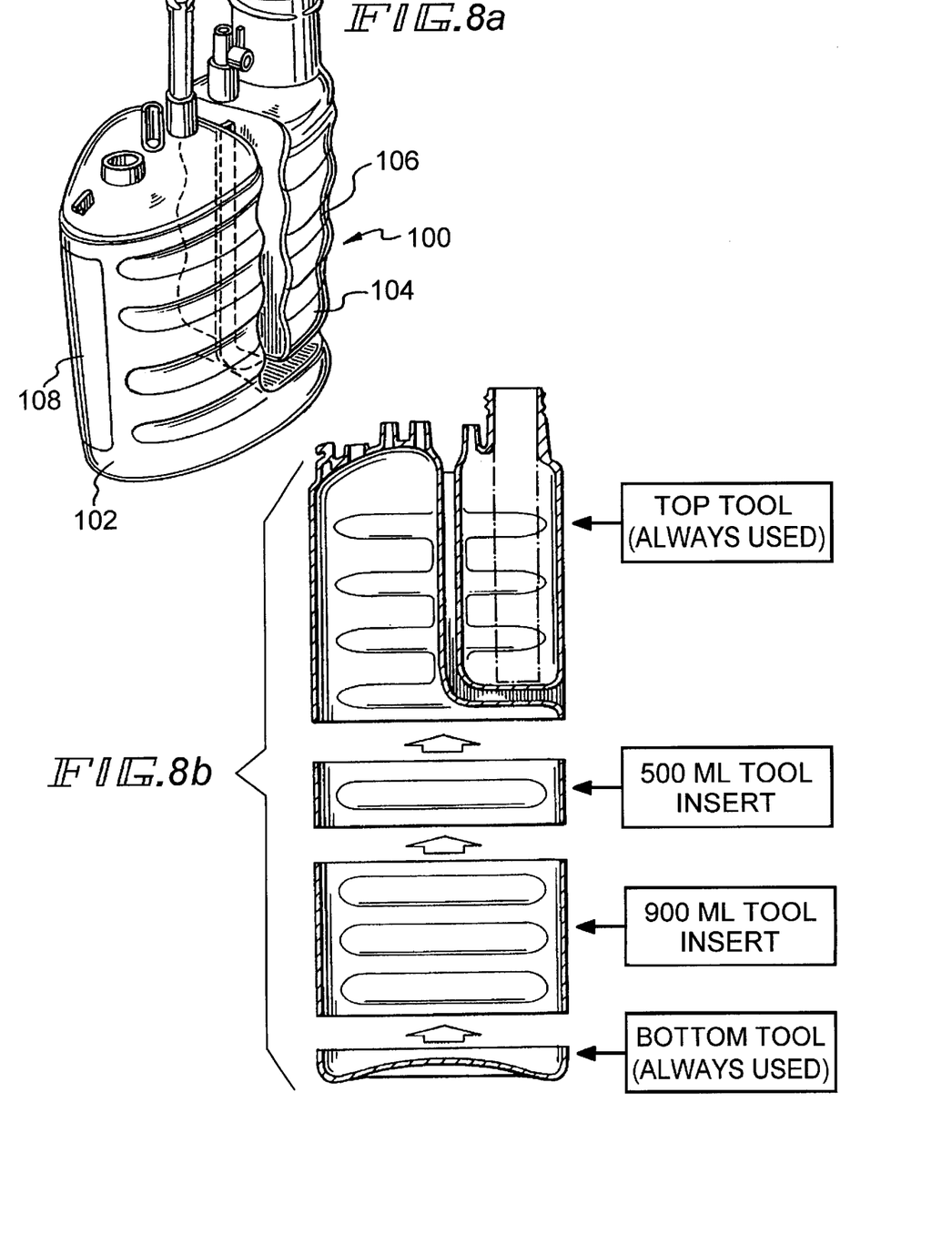
FIG. 8a shows a side elevational view of a further configuration for the container in accordance with the invention wherein the container is oval in plan view and includes two chambers, a vacuum chamber and a fluid chamber for collecting wound drainage fluids.
FIG. 8b shows a side elevational view of the container shown in FIG. 8a, illustrating how the container may be manufactured in three sizes having a nominal capacity of 350, 500 or 900 ml.
Figure 8C:
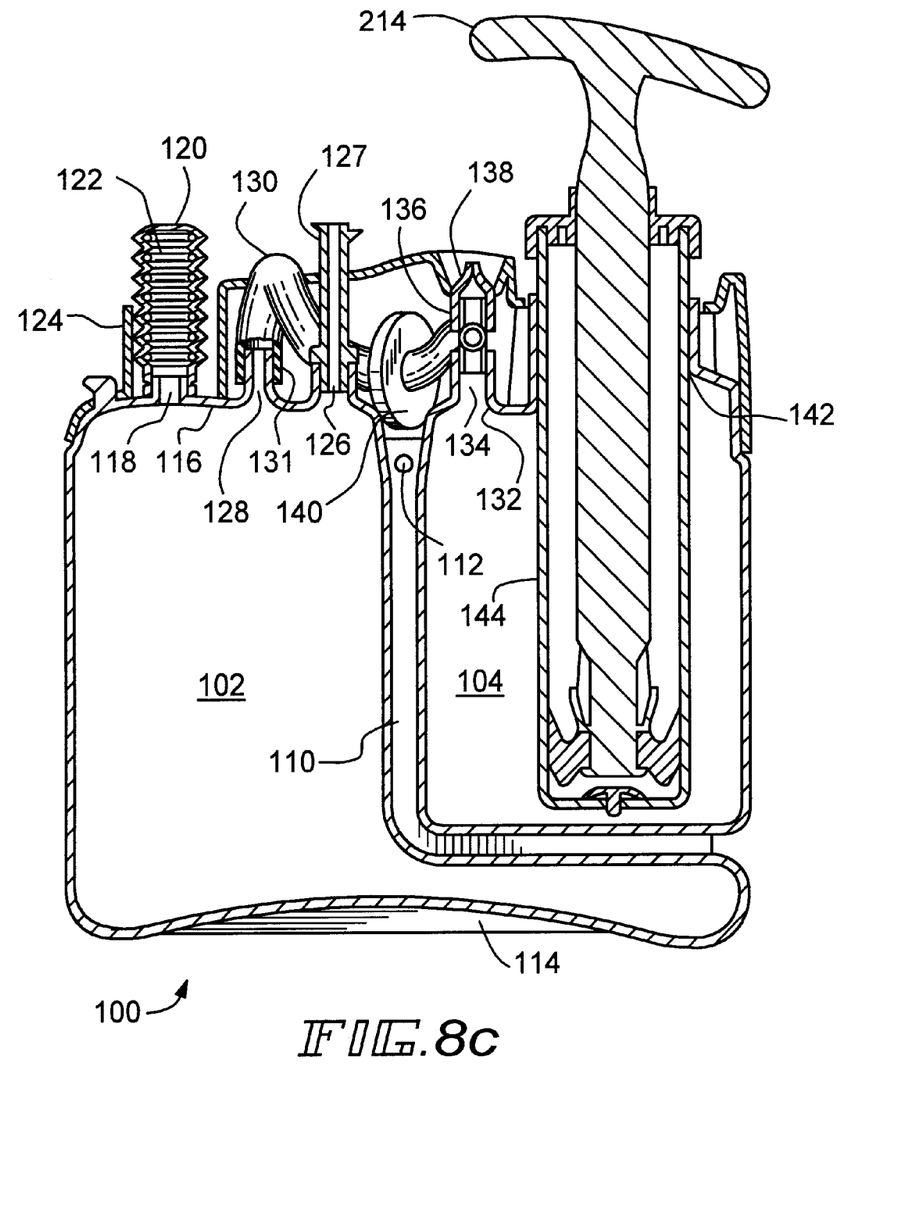
FIG. 8c shows a cross-sectional view of the container shown in FIG. 8a, illustrating the construction and the interconnection of the two chambers of the container.

FIGS. 8a–c illustrate another configuration of a preferred embodiment for a surgical wound drainage container in accordance with the invention. The container, generally indicated by the reference 100, includes a wound drainage fluid collection chamber 102 and a vacuum chamber 104. This embodiment, while marginally more expensive to produce provides several distinct advantages. First, wound drainage fluid is isolated from the vacuum chamber so the vacuum pump is never contaminated regardless of the volume of fluid collected in the wound drainage fluid collection chamber 102. Second, it is well known that in most commonly used wound drainage systems, the subatmospheric pressure decreases proportionally to the volume of collected fluid. This problem is eliminated by using a vacuum chamber 104 isolated from the wound drainage fluid collection chamber 102. The container 100 shown in FIG. 8a is preferably blow molded from a synthetic resin in a manner well known in the art. The sidewall of the container 100 is reinforced by smooth ribs 106 to provide strength under vacuum. The ribs 106 also provide an ergonomic grip to facilitate handling the container 100. An end of the wound drainage fluid collection chamber 102 also preferably includes a smooth area 108 in the form of a rectangular window which may be used to adhere a label or may be used for a marker to indicate, for example, the amount of fluid drained from a surgical wound on a daily basis.

FIG. 8b shows a schematic diagram of how various size wound drainage containers in accordance with this embodiment are constructed. The container is preferably manufactured in 350 ml, 500 ml and 900 ml sizes. In blow molding, the same tool is used for molding the top of all three sizes of the container. A single tool is used for molding a bottom of each container as well. To produce a 500 ml and a 900 ml container, additional inserts are provided to add the sections shown, as appropriate. Containers having different volumes can be manufactured using the same principles.

FIG. 8c shows a cross-sectional view of the container 100 in accordance with the invention. As explained above, the container 100 includes a wound drainage fluid collection chamber 102 and a vacuum chamber 104. The two chambers are interconnected by a compression molded web 110 formed during the blow molding process in a manner well known in the art. The compression molded web 110 preferably includes a hole 112 useful for suspending the container 100 when appropriate. A bottom of the container 100 preferably includes a compression molded rib 114 to reinforce the bottom against collapse when the container 100 is evacuated. This container, as in all containers in accordance with the invention, should withstand a vacuum of about 0.9 atmospheres without collapse.

The wound drainage fluid collection chamber 102 is provided with three integral cylindrical orifices molded in a top wall 116 of the container. A first orifice 118 supports a collapsible bellows 120 made of a resilient plastics material. The bellows 120 preferably includes a coil spring 122 which is tempered to support the bellows 120 in a manner that the bellows 120 provides an accurate measure of the subatmospheric pressure in the wound drainage fluid collection chamber 102. Surrounding the orifice 118 and the bellows 120 is a pressure gauge 124 which is embossed or printed with an indicia (not illustrated) for indicating the subatmospheric pressure in the fluid collection chamber 102. The pressure gauge 124 in combination with the bellows 120 will preferably accurately indicate a subatmospheric pressure of from about 0.1 to at least about 0.5 atmospheres. A second orifice 126 is provided 5 with a Luer Lock® connector 127 to which a wound drainage tube may be connected. The Luer Lock® connector 127 is preferably spun welded into a top of the orifice 126 after the molding process is complete. A third orifice 128 provides a connection for a vacuum tubing 130 which in turn is connected to the vacuum chamber 104. A vacuum tubing connector 131 is also preferably spun welded to a top of the vacuum tubing orifice 128 after blow molding is complete. The vacuum chamber 104 includes two orifices in its top wall 132. A T-connector 136 is spun welded to a vacuum orifice 134. The T-connector 136 provides a first connection for the vacuum tubing 130 and a second connector for a vacuum release valve 138, which is preferably a duck bill valve that permits the vacuum to be manually released and/or adjusted. The vacuum tubing 130 is preferably interrupted by a filter 140. The filter 140 is preferably a hydrophobic filter which inhibits the passage of fluids from the fluid collect on chamber 102 to the vacuum chamber 104. If the fluid collection chamber 102 overfills during a period when the vacuum system is unattended, the hydrophobic filter 140 prevents fluid from overflowing into the vacuum chamber 104. The filter 140 is also preferably bacreriostatic to prevent the migration of bacteria from fluid in the fluid collection chamber 102 to the vacuum chamber 104.

The second orifice 142 is adapted fear the connection of a vacuum pump barrel 144. It therefore preferably includes an external thread (not illustrated) which is integrally molded therewith for threadably engaging the vacuum pump barrel 144 to the vacuum chamber 104.

When a wound drainage tubing is connected to the Luer Lock~connector 127 and the vacuum pump is operated to induce a subatmospheric pressure in the vacuum chamber 104, air is withdrawn from the fluid collection chamber 102 and the induced vacuum causes the bellows 120 to compress, indicating the subatmospheric pressure induced. Fluid from the wound is then drawn through the wound drainage tubing (not illustrated) and the Luer Lock® connector 127 into the fluid collection chamber 102. The pump may be operated intermittently to maintain the subatmospheric pressure in the fluid collection chamber 102 at a preferred level in accordance with a regimen selected by the attending physician. Because the vacuum chamber 104 is isolated from the fluid collection chamber 102, an optimal subatmospheric pressure can be maintained in the fluid collection chamber 102 regardless of the volume of fluid collected. In most prior art wound drainage systems, the subatmospheric pressure declines proportionally with the amount of fluid collected in the fluid collection chamber. The prior art systems therefore frequently fail to provide optimal wound drainage throughout the post-operative period. As will be explained below in more detail with reference to FIG. 12, it has been discovered that an optimal regimen for wound drainage requires adjustment over time of the suction pressure applied to the wound.

Figures 9A, 9B:
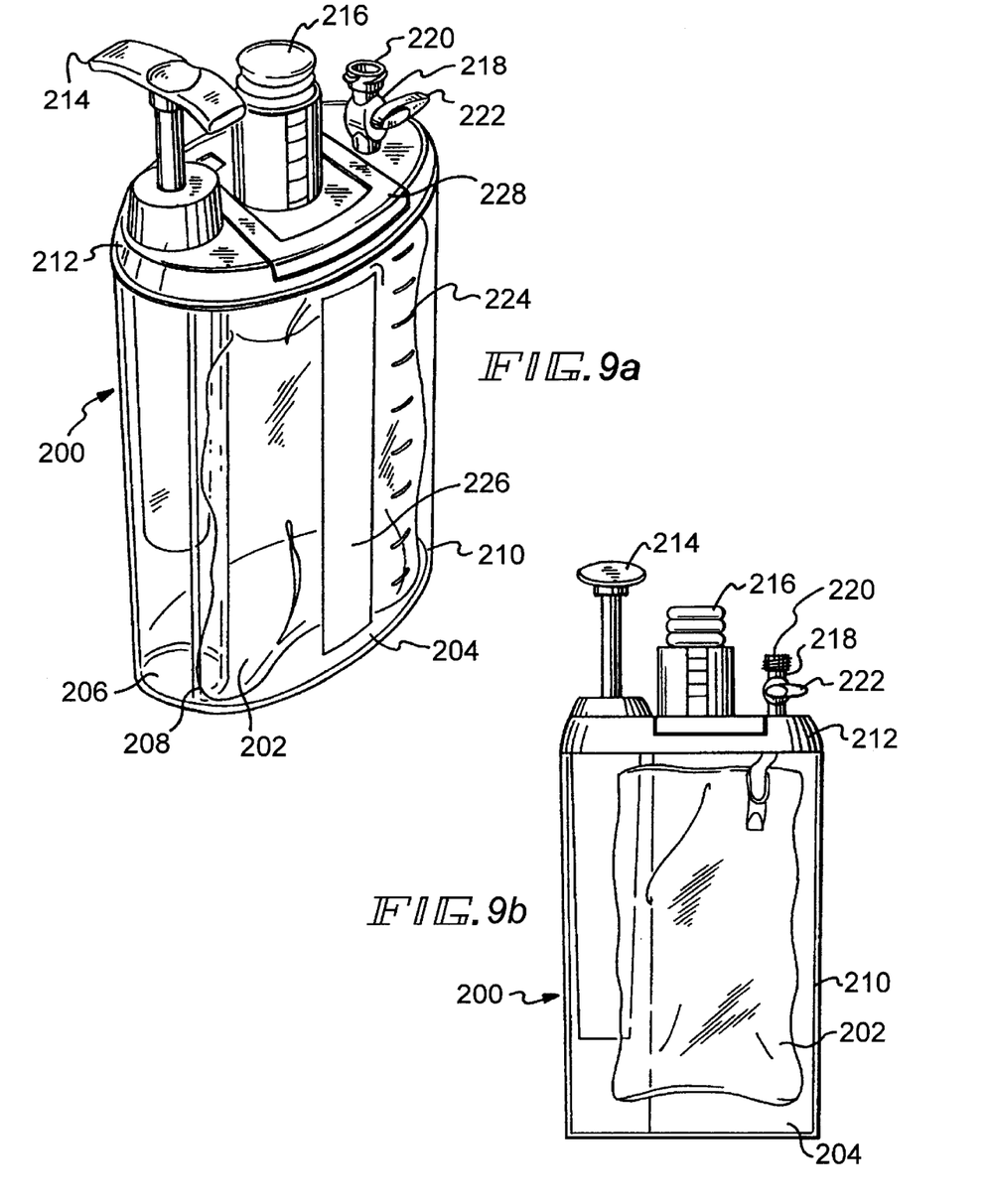

FIG. 9a is a perspective view of yet another configuration for a wound drainage container 200 in accordance with the invention. The container 200, unlike the containers described above, is intended to be reused. Wound drainage fluid is collected in a collapsible receptacle such as a blood bag 202 which is enclosed in a fluid collection chamber 204 that is segregated from a vacuum chamber 206 by a partition 208 that is integrally molded with a sidewall 210 of the container 200. The partition 208 includes an orifice (not illustrated) for establishing fluid communication between the vacuum chamber 206 and the fluid collection chamber 204. The orifice is preferably located near a top of the container 200 in order to prevent the migration of collected fluids from the fluid collection chamber 204 to the vacuum chamber 206 in the event that the blood bag 202 ruptures or otherwise discharges fluid. The container 200 includes a removable top cover 212 which preferably snaps on and off the sidewall 210 using a plastic interference joint in a manner known in the art. The top cover 212 is provided with an O-ring (not illustrated), or the like, to provide a fluid impervious seal in a manner well known in the art so that the container 200 can be evacuated to a subatmospheric pressure of at least 0.5 atmospheres. Mounted to the top cover 212 is a vacuum pump 214 of the type described above. Also mounted to the top cover 212 is a bellows gauge 216 of the type described in relation to FIG. 8c above. The bellows gauge 216 is constructed and functions in an identical manner with the bellows gauge described with reference to FIG. 8c. A bottom end of the bellows gauge 216 is in fluid communication with the fluid collection chamber 204. A wound drainage tube connector 218 is connected to and extends through the top cover 212. A lower end of the wound drainage tube connector 218 provides a connection for the blood bag 202. A top end of the wound drainage tube connector 218 includes a Luer Lock~connector 220 for the attachment of a wound drainage tube (not illustrated). The wound drainage tube connector 218 optionally includes a control valve 222 which may be operated to control fluid flow through the wound drainage tube connector 218. The sidewall 210 of the container 200 preferably includes an integrally molded or printed volume scale 224 to indicate the volume of liquid collected as well as a smooth rectangular write strip 226 which may be used to record the daily discharge collected in the container 200. The top cover 212 may also include a hinged hanger handle 228, or a similar attachment useful for suspending the container 200 when required.

FIG. 9b shows a side elevational view of the container 200. In use, the top cover 212 is removed from the container 200 and a fluid collection receptacle such as a blood bag 202 is connected to a bottom end of the wound drainage tube connector 218. The cover 212 is then replaced taking care that the blood bag 202 is suspended in the container 200 and not pinched or trapped between the container sidewall 210 and the container cover 212. The vacuum pump 214 is then operated to induce the desired subatmospheric pressure in the fluid collection chamber 204 as indicated by the bellows gauge 216 or by the number of pump strokes (see FIG. 12). If a control valve 222 is not provided on the wound drainage tube connector 218, the wound drainage tube is preferably connected to the wound drainage tube connector 218 before the vacuum pump 214 is operated. After the wound drainage tube has been connected to the wound drainage tube connector 218, the vacuum is adjusted if necessary by operating the vacuum pump 214 until the required subatmospheric pressure is established. When the blood bag 202 is full, or wound drainage is complete, the control valve 222 is closed, the wound drainage tube is disconnected, the cover 212 is removed from the container 200, the blood bag 202 is sealed with a clamp and disconnected from the wound drainage tube connector 218. The collected fluid may then be disposed of or, when appropriate, used for transfusion back to the patient after an appropriate treatment process, if necessary.

Figure 10A:
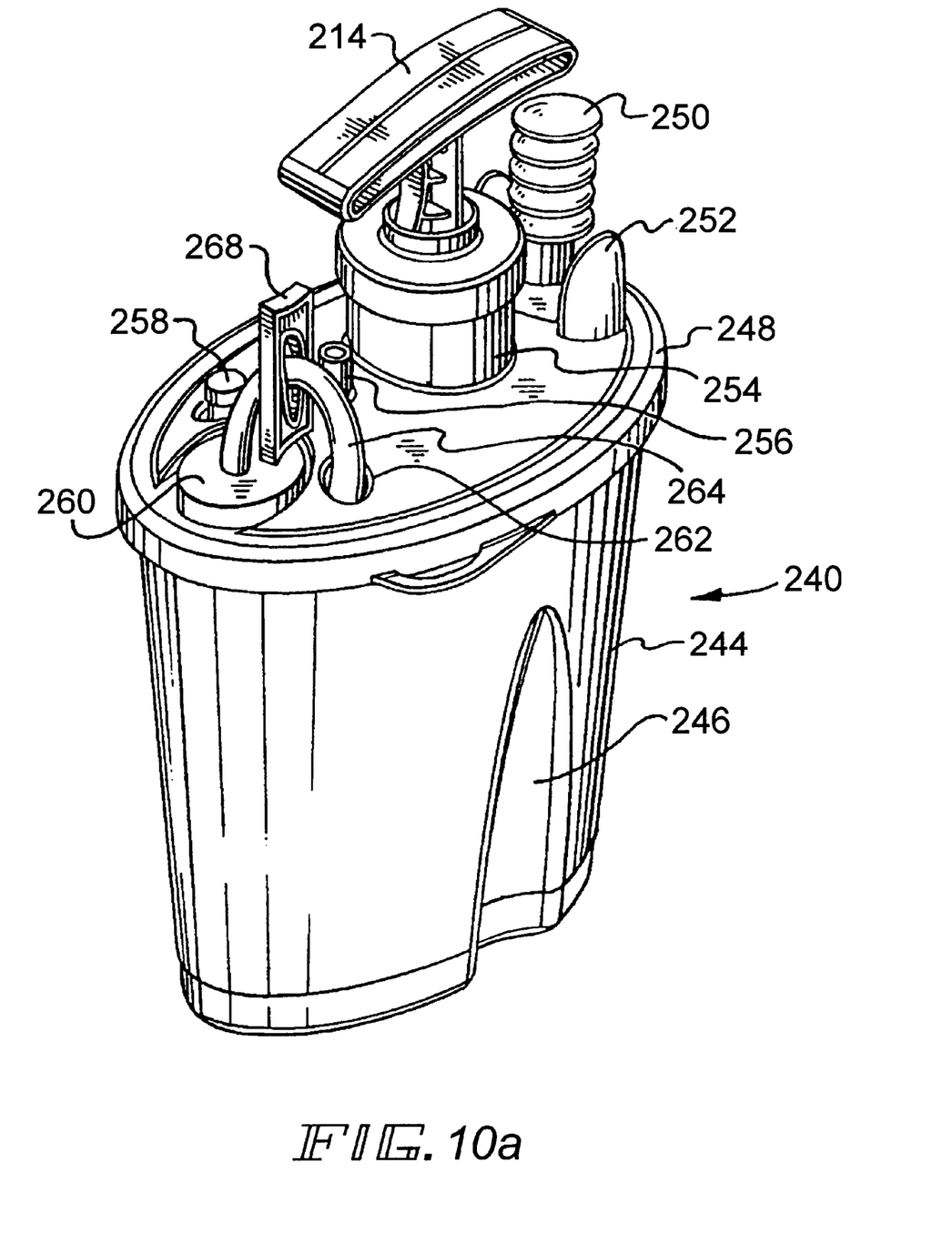
FIG. 10a shows a perspective view of another configuration for the container in accordance with the invention wherein a barrel of the vacuum pump extends into the fluid collection chamber but the pump is isolated front direct fluid communication from the fluid collection chamber.

FIG. 10a shows a perspective view of a further configuration for a wound drainage container 240 in accordance with the invention. The container 240, unlike the container 200 described above, is intended to be completely disposable. The assembled container 240 includes a drainage fluid collection chamber 242 (see FIG. 10b) defined by a sidewall 244 of the container 240. The sidewall 244 includes opposed vertical recessed areas 246 to facilitate gripping the container 240 when it is handled. A cover 248 is permanently bonded to the container sidewall 244 when the container 240 is assembled. The cover 248 includes integrally molded parts for supporting a bellows gauge 250, a bellows gauge guard 252, a pump barrel 254, a drainage tube connector 256, a pressure release valve 258, a hydrophobic filter 260 and a vacuum tubing orifice 262 which is adapted to accommodate a vacuum tubing 264, the arrangement of which will be explained in detail with relation to FIG. 10b. The pump barrel 254 supports a vacuum pump 214 the construction of which is described with reference to FIG. 11.

Figure 10B:
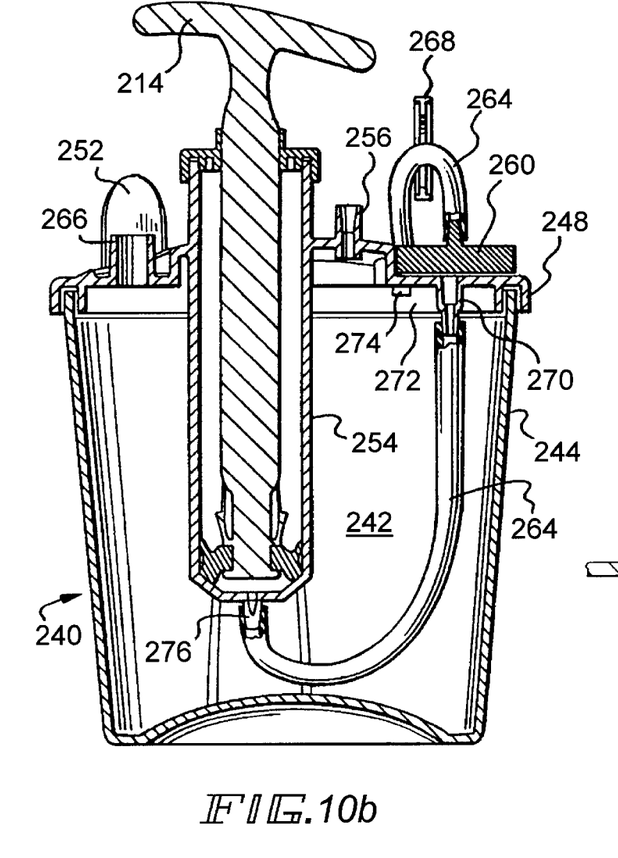

FIG. 10b shows a cross-sectional view of the container 240 shown in FIG. 10a. As explained above, the sidewall 244 of the container 240 defines a fluid collection chamber 242 which is preferably constructed to hold 300, 500 or 900 ml. The sidewall 244 is capped by the cover 248 which is molded to define the integral pump barrel 254 which accommodates the manual vacuum pump 214. Also integrally molded into the cover 248 are a filter connector 270 for connecting the hydrophobic filter 260, and a bellows gauge connector 266. A pump barrel 254 extends into the fluid collection chamber 242 when the cover 248 is mounted to the sidewall 244. The vacuum pump 214 is isolated from direct fluid communication with the fluid collection chamber 242 by the pliable vacuum tubing 264 which connects to a bottom end of the filter connector 270 which extends through a vacuum chamber 272 located above the fluid collection chamber 242 and integrally molded into the cover 248. On the opposite side of the hydrophobic filter 260 is another section of vacuum tubing 264 which connects the filter 260 to a vacuum port 274 that extends through the cover 248 into the vacuum chamber 272. A sliding clamp 268 is preferably provided on the exposed section of the vacuum tubing 264 to permit the vacuum tubing 264 to be closed when the container 240 is not being evacuated using the vacuum pump 214. The sliding lock 268 prevents the intrusion of drainage fluid through the vacuum chamber 272 and the vacuum tubing 264 into the hydrophobic filter 260 should the container 240 be accidently overturned for an extended period of time. As will be understood by those skilled in the art, the vacuum chamber 272 is provided with at least one path of fluid communication with the fluid collection chamber 242. That path in the form of a slot or one or more holes (not illustrated) is preferably sized to permit the ready passage of air but to inhibit the passage of wound drainage fluid from the fluid collection chamber 242 to the vacuum chamber 272. When the vacuum pump 214 is operated, air is drawn from the fluid collection chamber 242 through the vacuum chamber 272 and the vacuum tubing 264 and expelled to atmosphere around the pump handle. The bottom length of the vacuum tubing 264 is connected to a tubing connector 276 and the filter connector 270 before the cover 248 is applied to the sidewall 244 of the container 240. The cover 248 is preferably attached to the sidewall 244 using an adhesive effective with the plastic material of which the disposable container 240 is constructed.

To use the container 240, it is placed on a flat surface and the sliding clamp 268 is released to permit the container 240 to be evacuated and a wound drainage tubing is attached to the wound drainage tubing connector 256, which may, for example, be a Luer Lock~connector. The manual vacuum pump 214 is then operated the number of strokes required to evacuate the container 240 to the desired target subatmospheric pressure. The bellows gauge 250 (see FIG. 10a) provides at least a qualitative gauge of the subatmospheric pressure in the container 240. The bellows gauge guard 252 may be graduated with an index to provide a quantitative measure of the subatmospheric pressure in the container 240. This container 240 is designed to be disposable. If it becomes full before wound drainage is complete, it may be emptied into a suitable receptacle by releasing any residual vacuum using the pressure release valve 258 and disconnecting the wound drainage tubing from the drainage tube connector 256. A drainage tube connected to a suitable receptacle is then connected to the drainage tube connector 256, the sliding clamp 268 is moved to the locked position to close the vacuum tubing 264 to ensure that fluid does not flow into the hydrophobic filter 260 and the container 240 is inverted to drain fluid from the container 240. To facilitate drainage, the vacuum release valve 258 may be opened slightly to permit air to enter the container 240 as fluid is displaced.

Figure 11:
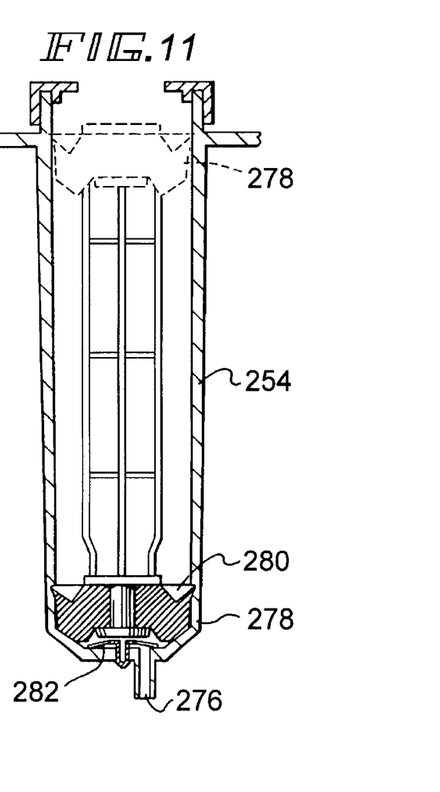
FIG. 11 shows a cross-sectional view of a disposable vacuum pump designed especially for the containers in accordance with the invention.

FIG. 11 shows a cross-sectional views of the stroke of the pump 214, which was designed expressly for use with disposable containers in accordance with the invention. Manual vacuum pumps such as disclosed in U.S. Pat. No. 4,889,250 are generally considered too expensive to be disposed of with containers. A pump having a novel piston 278 made of a resilient material such as neoprene rubber is configured with an upwardly directed, flared skirt 280 which is shaped to closely conform to the inner surface of the pump barrel 254. When the pump is stroked upwardly, the flared skirt 280 forms a seal with the barrel 254 and draws air upwardly through the vacuum tubing connector 276 past an umbrella valve 282. When the pump reaches a top of its stroke shown in ghost lines at the top of the figure, the umbrella valve 282 closes the orifice in the tubing connector 276 and as the pump piston 278 is returned to the bottom of the barrel 254, the skirt 280 collapses inwardly and the air is expelled from the pump barrel 254. This novel manual vacuum pump permits the commercial production at reasonable cost of a wound drainage container that is completely disposable.

Figure 12:
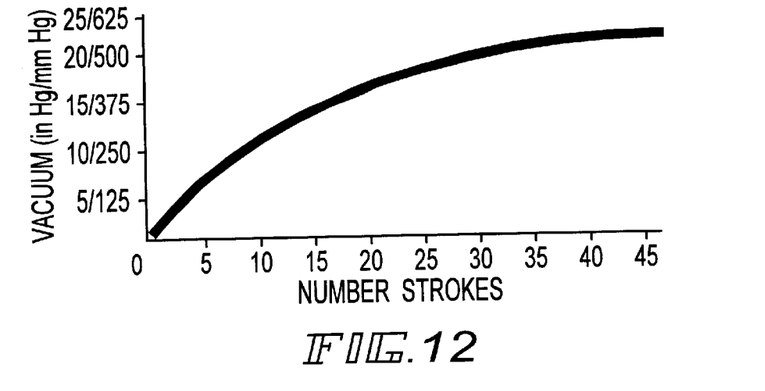
FIG. 12 is a graphical representation showing the relationship between the average number of pump strokes and the vacuum in inches and millimeters Hg.

FIG. 12 shows a graphic representation of the vacuum in inches and millimeters of mercury induced in the containers in accordance with the invention in relation to the number of strokes that the vacuum pump is operated. On average, a subatmospheric pressure of about 550 mm Hg is induced with about 45 pump strokes depending on the size and model of the container to which the pump is attached. As is apparent, very little effort is required to maintain a desired vacuum when using a wound drainage system in accordance with the invention.

Figure 13:
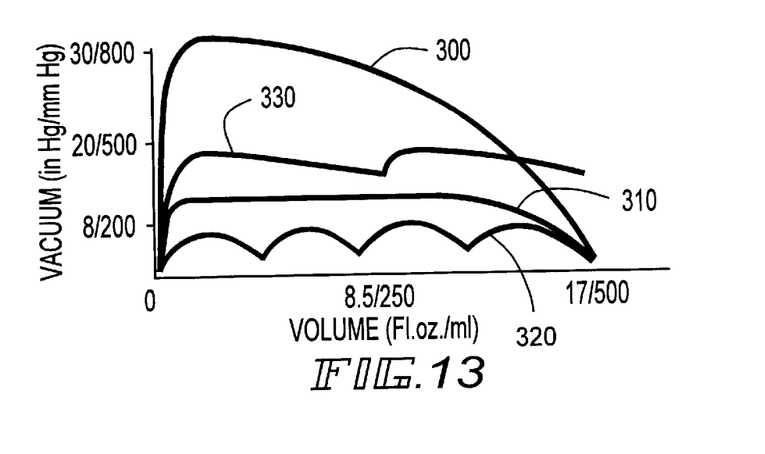
FIG. 13 shows a graphical representation of the vacuum in inches and millimeters Hg in relation to volume provided by certain wound drainage containers known in the prior art as well as containers in accordance with the invention.

FIG. 13 shows a graphic representation of the subatmospheric pressure in inches Hg and millimeters Hg in relation to the volume of fluid collected in a vacuum container. A line 300 is an approximation curve of the vacuum in a precharged, high vacuum container such as disclosed in U.S. Pat. No. 4,642,093 to Harle. As is apparent, the subatmospheric pressure in the container is very high when the container is first connected to a wound drainage tubing, assuming that the connection is perfectly executed and that the vacuum is not lost during the process. The vacuum thereafter declines steadily as fluid is drained from the wound and is substantially zero when the nominal capacity of the container is reached. Line 310 represents the relationship between volume and the vacuum in a precharged low vacuum container such as one taught by Harle. In general, the vacuum in low vacuum precharged containers is more steady than in high vacuum containers because those containers generally are precharged to a high vacuum (about 800 mm Hg) but the vacuum is reduced to approximately 200 mm Hg by a pressure reduction valve in the wound drainage tube connector of the container. Line 320 represents the vacuum curve of a compressible container such as taught in U.S. Pat. No. 3,993,080 to Loseff. As is apparent, such containers require frequent work and provide inconsistent vacuum. Line 330 is exemplary of a vacuum curve provided by a container in accordance with the invention. The shape of the curve will depend on the frequency with which the vacuum is recharged using the manual pump but in general, any level of vacuum including the high vacuum of up to about 800 mm Hg can be achieved and maintained until the nominal capacity of fluid is collected in the container. Unlike the prior art portable systems wherein vacuum universally decreases to near zero as the nominal capacity of the container is approached, the container in accordance with the invention provides up to a maximum vacuum until such time as nominal capacity is reached and the wound drainage tubing is disconnected from the container.

Figure 14:
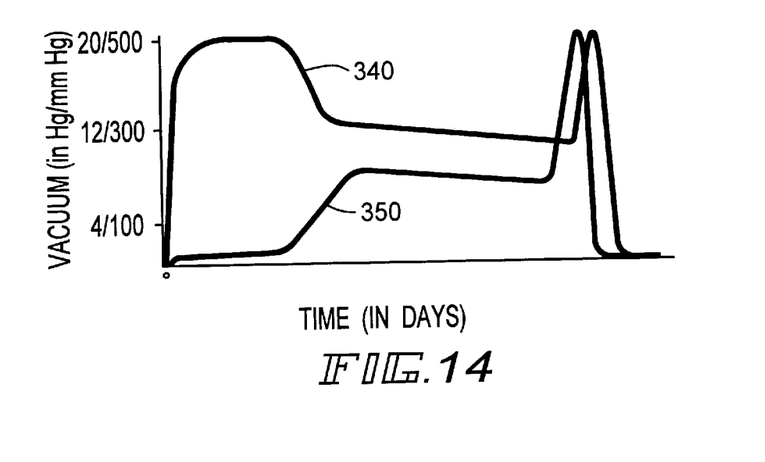
FIG. 14 shows a graphical representation of an optimal regimen for draining surgical wounds in both hard and soft tissues.

FIG. 14 shows a graphic representation of two optimal wound drainage regimens which can be practiced using a wound drainage system in accordance with the invention. The horizontal axis of the graph shows time in days while the vertical axis of the graph shows vacuum in inches and millimeters Hg. Line 340 represents an optimal wound drainage regimen for a surgical wound located in hard tissue such as striated muscle. In accordance with the optimal regimen, the wound drainage container is evacuated to a subatmospheric pressure of about 500 mm Hg as soon as the wound drainage tube is implanted and the container is connected. A high pressure is maintained in the container for the first post-operative day. After the first day, the vacuum is adjusted to about 300 mm Hg. That pressure is gradually decreased over the next three days until the pressure has reached about 250 mm Hg. Normally, wound drainage is ceased at about the fourth post-operative day. Prior to removing the drain from the surgical wound, the cavity is preferably evacuated to at least 500 mm Hg to avoid any residual fluid leaks around the fistula following the drain removal. After a few minutes at high vacuum, the vacuum is released and the drain is removed from the surgical wound.

Line 350 represents the optimal regimen for draining a surgical wound located in the soft tissue. During the first day, a very low vacuum of about 25 mm Hg is maintained to enhance the soft tissue repair process. At the end of the first post-operative day, the vacuum is gradually increased until the vacuum reaches about 200 mm Hg and that vacuum is maintained with a slight gradual decrease until about three and a half days when the pressure is increased to a maximum of about 500 mm Hg for a brief period of time before the drain is removed to avoid residual fluid leak via the fistula, as described above. Other regimens may also be found to be particularly effective for a given surgical wound. Any normal regimen can readily be followed, however if a wound drainage container in accordance with the invention is used during post operative treatment.

The wound drainage systems in accordance with the invention permit the practice of an optimal regimen based on the type of tissue in which the surgical wound is located. Because of the degree of control which can be achieved using the wound drainage systems in accordance with the invention, it is not only possible but practical to adhere closely to an optimal regimen, thus facilitating the readaptation of damaged tissue and the healing process.

Changes and modifications to the embodiments described may be made by those skilled in the art without departing the spirit of the invention, which is intended to be limited solely by the scope of the appended claims.

I claim:

1. A surgical wound drainage apparatus for removing and collecting fluids from a closed wound comprising: a rigid container having a top, a vacuum chamber and a fluid collection chamber, the fluid collection chamber being in fluid communication with the vacuum chamber; a manual vacuum pump mounted to the top of the container, the manual vacuum pump being in fluid communication with the vacuum chamber and having a pump barrel that extends into the fluid collection chamber, and a tubing interconnects a bottom end of the pump barrel with the vacuum chamber so that the pump is in fluid communication with the vacuum chamber but there is no fluid communication between the pump and the fluid collection chamber; and at least one connector adapted for the connection of a surgical drainage tubing in fluid communication with the fluid collection chamber.

2. A surgical wound drainage apparatus for removing and collecting fluids from a closed wound as claimed in claim 1 wherein the vacuum chamber is located above the fluid collection chamber in a cover of the container.

3. A surgical wound drainage apparatus for removing and collecting fluids from a closed wound as claimed in claim 2 wherein a hydrophobic filter is connected in line with the tubing between the pump barrel and the vacuum chamber.

4. A surgical wound drainage apparatus for removing and collecting fluids from a closed wound as claimed in claim 3 wherein a portion of the tubing between the hydrophobic filter and the vacuum chamber is exposed on an outside of the container and is provided with a clamp for sealing the tubing during periods when the pump is not being operated to evacuate the container to ensure that collected fluid does not migrate to the filter if the container is accidentally inverted during such periods.

5. A surgical wound drainage apparatus for removing and collecting fluids from a closed wound comprising: a rigid container having a top, a vacuum chamber and a fluid collection chamber, the fluid collection chamber being in fluid communication with the vacuum chamber; a manual vacuum pump mounted to the top of the container, the manual vacuum pump being in fluid communication with the vacuum chamber, at least a portion of the manual vacuum pump being disposed within the vacuum chamber, and a fluid communication path between the vacuum chamber and the fluid collection chamber including a hydrophobic filter to prevent collected fluids from migrating from the fluid collection chamber to the vacuum chamber; and at least one connector adapted for the connection of a surgical drainage tubing in fluid communication with the fluid collection chamber.

6. A surgical wound drainage apparatus for removing and collecting fluids from a closed wound comprising:

a rigid container having a vacuum chamber and a fluid collection chamber, the fluid collection chamber being in fluid communication with the vacuum chamber;

a manual vacuum pump mounted to a top of the container so that a portion of the vacuum pump is disposed within the vacuum chamber, the manual vacuum pump being in fluid communication with the vacuum chamber;

a fluid communication path between the vacuum chamber and the fluid collection chamber including a hydrophobic and bacteriostatic filter to prevent collected fluids from migrating from the fluid collection chamber to the vacuum chamber and to inhibit contamination of the atmosphere with airborne infectious agents when the vacuum pump is operated;

at least one connector adapted for the connection of a surgical drainage tubing so that the tubing is in fluid communication with the fluid collection chamber when it is connected to the connector; and a pressure relieve valve in fluid communication with a one of the vacuum chamber and the fluid collection chamber to permit vacuum within the chambers to be released on demand.

7. A surgical wound drainage apparatus for removing and collecting fluids from a closed wound comprising:

a rigid container having a vacuum chamber and a fluid collection chamber, the fluid collection chamber being in fluid communication with the vacuum chamber;

a removable cover which is selectively removable from the rigid container, the removable cover providing a fluid tight seal with the vacuum chamber and the fluid collection chamber when the removable cover engages a top of the rigid container;

a manual vacuum pump mounted to the removable cover, the manual vacuum pump being in fluid communication with the vacuum chamber when the removable cover engages the top of the rigid container;

the fluid collection chamber being adapted to accommodate a fluid collection bag connectable in a fluid tight relationship with a connector adapted for the connection of a surgical drainage tubing so that the tubing is in fluid communication with only the fluid collection bag;

whereby operation of the manual pump when the removable cover engages the top of the rigid container induces a vacuum in the fluid collection chamber which is transmitted via the fluid collection bag to the surgical drainage tubing causing fluids to drain from the wound and collect in the fluid collection bag.

8. A surgical wound drainage apparatus for removing and collecting fluids from a closed wound as claimed in claim 7 wherein the container further includes a pressure gauge in fluid communication with a one of the vacuum chamber and the fluid collection chamber, but not in fluid communication with the fluid collect on bag.

9. A surgical wound drainage apparatus for removing and collecting fluids from a closed wound as claimed in claim 8 wherein the pressure gauge is a bellows gauge.

* * * * *